United States Patent [19]

Tanaka

[11] Patent Number: 5,690,110

[45] Date of Patent: Nov. 25, 1997

[54] ULTRASOUND SCANNER HEAD

[75] Inventor: Toshizumi Tanaka, Omiya, Japan

[73] Assignee: Fuji Photo Optical Co., Ltd., Omiya, Japan

[21] Appl. No.: 601,506

[22] Filed: Feb. 14, 1996

[30] Foreign Application Priority Data

Feb. 17, 1995 [JP] Japan ................................. 7-052035

[51] Int. Cl.⁶ .................................................. A61B 8/00
[52] U.S. Cl. .................................................. 128/660.1
[58] Field of Search .. 33/772–782; 128/660.08–660.09, 128/662.03; 73/635–639

[56] References Cited

U.S. PATENT DOCUMENTS 4,458,689  7/1984  Sorenson et al. ................... 128/661.01

FOREIGN PATENT DOCUMENTS 3224037  12/1983  Germany ................... 128/660.09

*Primary Examiner*—Francis Jaworski
*Attorney, Agent, or Firm*—Oblon, Spivak, McClelland, Maier & Neustadt, P.C.

[57] ABSTRACT

A mechanical scan type ultrasound scanner head for ultrasound examination systems, which is capable of detecting the position or distance of movement of an ultrasound transducer in mechanical scanning operations, and which includes: an ultrasound scanner head assembly movable along a subject to be scanned; an ultrasound transducer element mounted on the ultrasound scanner head assembly to transmit and receive ultrasound signals at predetermined intervals in travel distance along the subject; a rotary tracking member mounted on the scanner head assembly in the proximity of the ultrasound transducer element and rotatable at a rate commensurate with the distance of movement of the ultrasound transducer element; and a position measuring means connected to the rotary tracking member to measure the distance of travel of the ultrasound transducer element from an initial position of a scanning operation by way of a rotational angle of the rotary tracking member.

10 Claims, 7 Drawing Sheets

ULTRASOUND SCANNER HEAD

BACKGROUND OF THE INVENTION

Field of the Art

This invention relates to an ultrasound scanner head for use with ultrasound examination systems, and more particularly to an ultrasound scanner head of the so-called mechanical scan type which carries an ultrasound transducer and which is mechanically or manually put in a scanning motion along a subject of interest, while transmitting and receiving ultrasound signals through the transducer at predetermined intervals in travel distance to obtain a tomographic ultrasound image of the subject for examination or diagnostic purposes.

As well known in the art, in mechanical scan type ultrasound examination systems, generally a scanner head with an ultrasound transducer element is moved manually or by means of a powered drive mechanism extracorporeally along an outer skin surface or intracorporeally along an intracavitary wall of a subject of ultrasound examination, transmitting ultrasound pulses toward an intracorporeal region of interest through the ultrasound transducer element and at the same time receiving return echoes from internal tissues in a tomographic scanning range. Upon reception by the ultrasound transducer element, return echo signals are converted into electrical signals and transferred to an ultrasound image observation terminal which displays tomographic ultrasound images on a monitor screen after predetermined signal processing operations well known in the art.

In this connection, when an ultrasound transducer element is mechanically moved as in a mechanical scanning operation just described above, it is necessary to continually detect the position or distance of movement of the ultrasound transducer in relation to the mechanical scanning movement. Namely, in order to control the ultrasound signal transmissions and receptions, which should take place at predetermined intervals in travel distance of an ultrasound transducer element on an ultrasound scanner head, it is a matter of utmost necessity for a scanner of this sort to be able to detect the position of the transducer element constantly and correctly in terms of a travel distance from an initial position in each scanning operation. Besides, data of scanning positions are also necessary for each one of acoustic lines to be supplied successively to a scan converter on the basis of received ultrasound echo signals, because accurate ultrasound images cannot be produced without data of scanning positions. In this sense, in a mechanical ultrasound scanning operation, it is essential to detect the position or the distance of travel of the ultrasound transducer element in relation with its movement.

In this regard, according to typical prior art arrangement, an ultrasound transducer element is mounted on a movable block which is driven from a motor or other drive mechanism for a travel along a suitable guide means, while detecting the position of the transducer element by way of position signals produced on the basis of the number of revolutions of the drive motor or on the basis of movement of the transducer element along the guide means. In case of a manual ultrasound scanner, it has been the usual practice to connect to a scanner head to a manual operating means which can be manually pushed in and out to move an ultrasound transducer element on the scanner, detecting the transducer position by way of position signals which are produced on the basis of the amount of displacement of the manually operating means.

In the case of an ultrasound scanner assembly employing a drive motor or a similar drive mechanism for an ultrasound transducer as mentioned above, the scanner head needs to include at least a drive means, a movable carriage block connected to the drive means, a guide means for the carriage block, and a detector means for detection of the position of an ultrasound transducer element on the carriage block. Accordingly, scanners of this sort are usually objectionably complicated in construction and large in size, in addition to which the range of scanning operation by an ultrasound transducer element is restricted by the operational range of the guide means. Besides, in the case of an ultrasound scanner which is arranged to detect the position of an ultrasound transducer element by way of the amount of displacement of a manually operating means as mentioned above, a problem is also encountered in that the provision of such a manually operating means becomes a bar to downsizing the scanner assembly. Another problem with a mechanical scanner of this sort is that errors are likely to occur in determining the position of an ultrasound transducer element because what is detected by the detector is not the movement of the ultrasound transducer itself but the displacement of the manually operating means.

SUMMARY OF THE INVENTION

With the foregoing situations in view, the present invention has as its object the provision of a mechanical scan type ultrasound scanner head which is suitable for use with ultrasound examination systems, and which is capable of detecting position or movement of an ultrasound transducer correctly by the use of a simple tracking mechanism.

In accordance with the present invention, the above-stated objective is achieved by the provision of a mechanical scan type scanner head for ultrasound examination systems, the scanner head essentially including: an ultrasound scanner head assembly movable along a subject to be ultrasonically scanned; an ultrasound transducer element mounted on the ultrasound scanner head assembly to transmit and receive ultrasound signals at predetermined intervals in travel distance along said subject; a rotary tracking member mounted on the scanner head assembly in the proximity of the ultrasound transducer element and rotatable at a rate commensurate with the distance of movement of the ultrasound transducer element; and a position measuring means connected to the rotary tracking member to measure the distance of movement of the ultrasound transducer element from an initial position of a scanning operation by way of a rotational angle of the rotary tracking member.

With an ultrasound scanner head of the arrangements just described, the scanner head assembly which supports the ultrasound transducer element and the rotary tracking member are initially positioned on a subject to be scanned, for example, extracorporeally in abutting engagement with an outer skin surface of an intracorporeal region to be scanned. As the scanner head is moved from the initial position to make a scan in a certain direction, the rotary tracking member is simultaneously turned to follow the movement of the scanner head. During this movement of the scanner head, the position and distance of movement of the ultrasound transducer element are measured by the position measuring means on the basis of rotational angles of the rotary tracking member. Accordingly, the transmission of ultrasound pulses into the body of the subject can be controlled to take place at predetermined intervals in travel distance of the ultrasound transducer element, by supplying transmission drive signals thereto on the basis of position signals from the position measuring means. Of course, the positions signals from the position measuring means are also useful in determining the positions of return echo signals which are received as a result of the intermittent ultrasound pulse transmissions.

The above-mentioned rotary tracking member and position measuring means can be realized in various forms as will be described in greater detail hereinlater.

BRIEF DESCRIPTION OF THE DRAWINGS

The above and other objects, features and advantages of the invention will become apparent from the following particular description of the invention, taken in conjunction with the accompanying drawings which show by way of example preferred embodiments of the invention and in which.

PARTICULAR DESCRIPTION OF THE INVENTION

Figure 1:
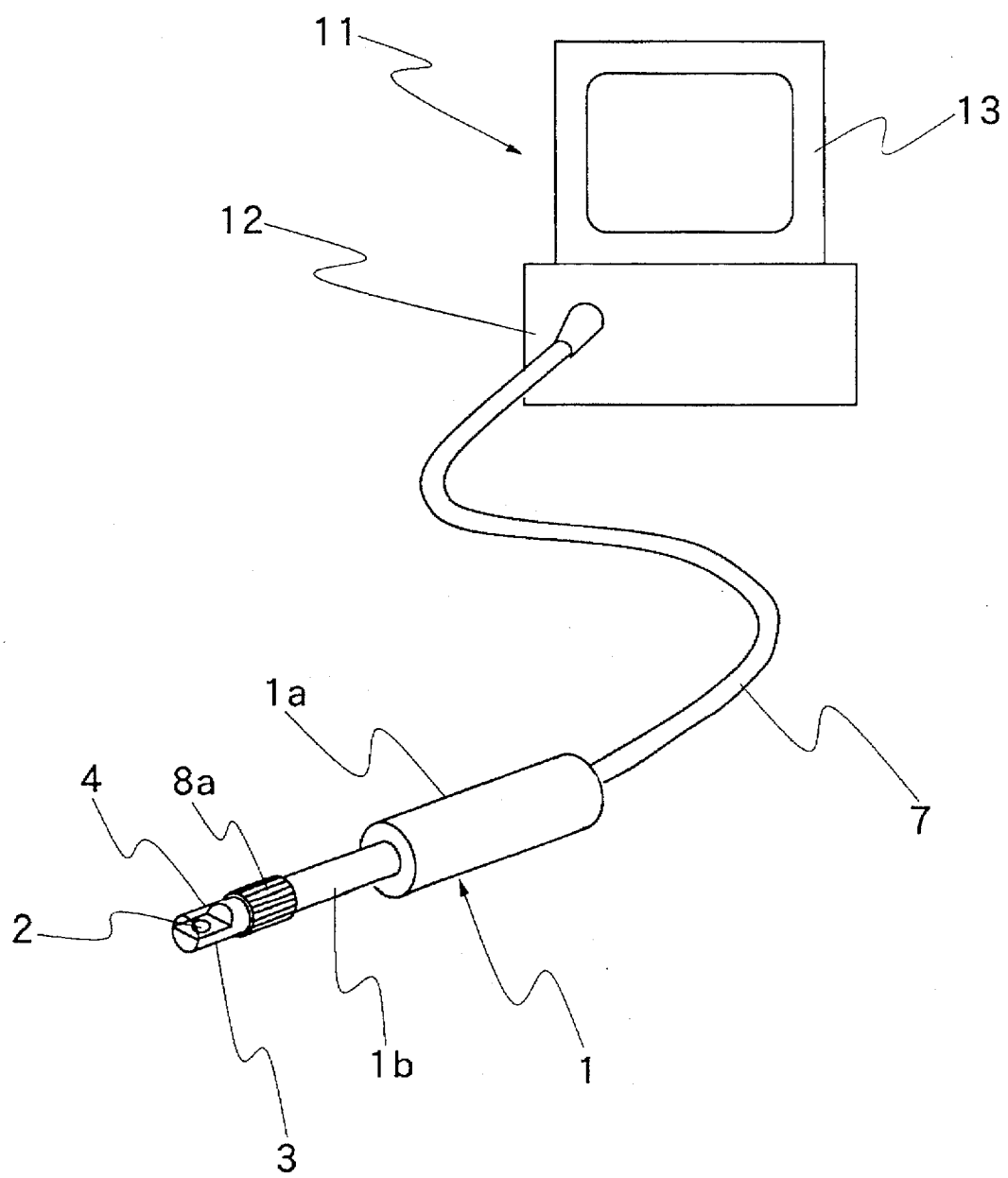
FIG. 1 is a schematic illustration, showing general layout of an ultrasound examination system incorporating an ultrasound scanner head according to the present invention.
Figure 2:
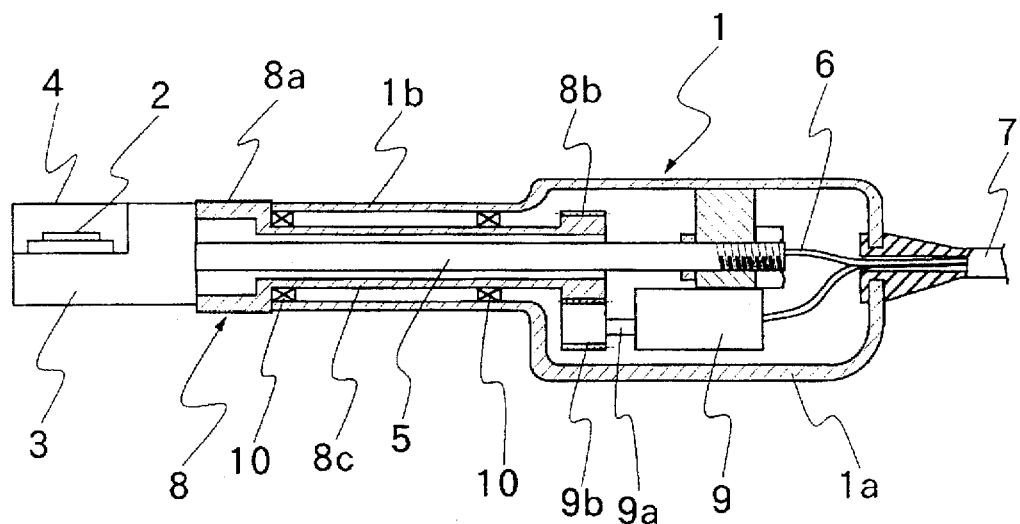
FIG. 2 is an enlarged sectional view of the scanner head shown in FIG. 1 as a first embodiment of the invention.

Referring to FIGS. 1 through 4, there is shown a first embodiment of the ultrasound scanner head according to the present invention. In FIGS. 1 and 2, indicated at 1 is a scanner head assembly which is housed in a casing 1a with a tubular fore extension 1b. Fixedly mounted at the fore end of the tubular extension 1b is a nesting base 3 which supports thereon an ultrasound transducer element 2 securely within a cap member 4 of an ultrasound transmissive material. The cap member 4 is fitted liquid-tight around the nesting base 3, and, in this instance, liquid paraffin or other acoustic material is sealed in the cap member 4. Securely connected to the nesting base 3 is a hollow connector rod 5 which is extended through the tubular extension 1b and the main casing 1a and fixedly supported at its rear end within the scanner head casing 1a. A signal cable 6 from the ultrasound transducer element 2 is passed through the internal cavity of the hollow connector rod 5 and led out of the scanner head assembly 1 through an external cable 7.

The above-described connector rod 5 is passed through a hollow rotational shaft 8 which is provided with, at the fore and rear ends of its hollow cylindrical body 8c, a tracking roller portion 8a to be turned by contact with skin surfaces of a subject when the scanner head is moved therealong, and a transmission gear 8b, respectively. The tracking roller portion 8a is loosely fitted in an exposed state between the fore tubular extension 1b and the nesting base 3, the exposed circumferential surface of the tracking roller portion 8a being knurled or laminated with a layer of a frictional material having a large friction coefficient like rubber so that the tracking roller portion 8a is turned securely in contact with body surfaces of a subject without slip in following the movement of the scanner head 1. The hollow tubular body 8c of the rotational shaft 8 is slidably fitted in the tubular fore extension 1b of the scanner head assembly 1. The transmission gear 8b at the rear end of the rotational shaft 8 is meshed with an input gear 9b on an input shaft 9a of an encoder 9 within the main casing 1a of the scanner head 1. A belt transmission or other form of transmission mechanism may be employed in place of the above-described gear transmission mechanism if desired.

Indicated at 11 is an ultrasound image observation terminal which is largely constituted by a signal processor 12 and a monitor 13 with a viewing screen. The external cable 7 from the ultrasound scanner head 1 is disconnectibly connected to the signal processor 12 on the ultrasound image observation terminal 11, which is arranged as shown diagrammatically in FIG. 3. In this figure, indicated at 14 is a signal transmission circuit, and at 15 a signal reception circuit. In a scanning operation, these signal transmission and reception circuits 14 and 15 are alternately or selectively connected to ultrasound transducer element 2 by a switch means 16. In signal transmission phases of operation, the ultrasound transducer element 2 is connected to and driven from the transmission circuit 14 to transmit a ultrasound pulse signal toward an intracorporeal region under observation. On the other hand, in signal reception phases of operation, the ultrasound transducer element 2 is connected to the reception circuit 15, supplying the latter with electrical signals corresponding to received ultrasound echo signals. The electrical signals are processed into video signals through predetermined signal processing operations for production of an ultrasound image. The video signals from the reception circuit 15 are sequentially fed to a frame memory of a digital scan converter 17 for sequentially framing input video signals of ultrasound image. From the digital scan converter 17, video signals are output frame by frame to the monitor 13 through an output circuit 18 to display ultrasound images on the monitor screen.

As the ultrasound transducer element 2 on the scanner head 1 is manually moved for a mechanical linear scan, the position or the distance of movement of the transducer element 2 is detected by the encoder 9 which picks up the movement of the transducer element 2 from an initial or starting position of the linear scanning operation. More specifically, in this embodiment, the above-described encoder constitutes a position detector means for the ultrasound transducer element 2. The encoder 9 is connected to a position detector circuit 19 which, on the basis of a signal of rotational angle from the encoder 9, produces a signal indicative of the position or the distance of movement of the transducer element 2. The output signal of the position detector circuit 19 is fed to the switch means 16 which controls the connection of the transducer element 2 with the signal transmission and reception circuits as described hereinbefore, and at the same time to the digital scan converter 17 as a position signal of the corresponding acoustic line.

In an operation for extracorporeally scanning an internal region of a patient, for example, the ultrasound scanner head of the first embodiment of the invention, with the above described arrangements, is operated in the manner as follows.

Figure 4:
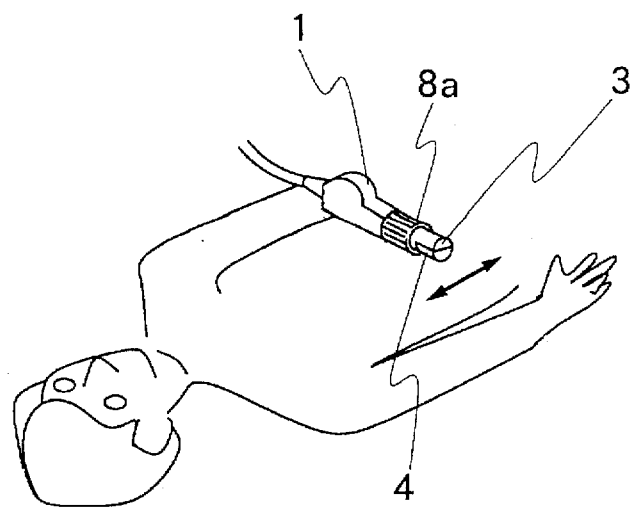
FIG. 4 is a schematic illustration of a scanning operation by the use of the ultrasound scanner head of the first embodiment.
Figure 3:
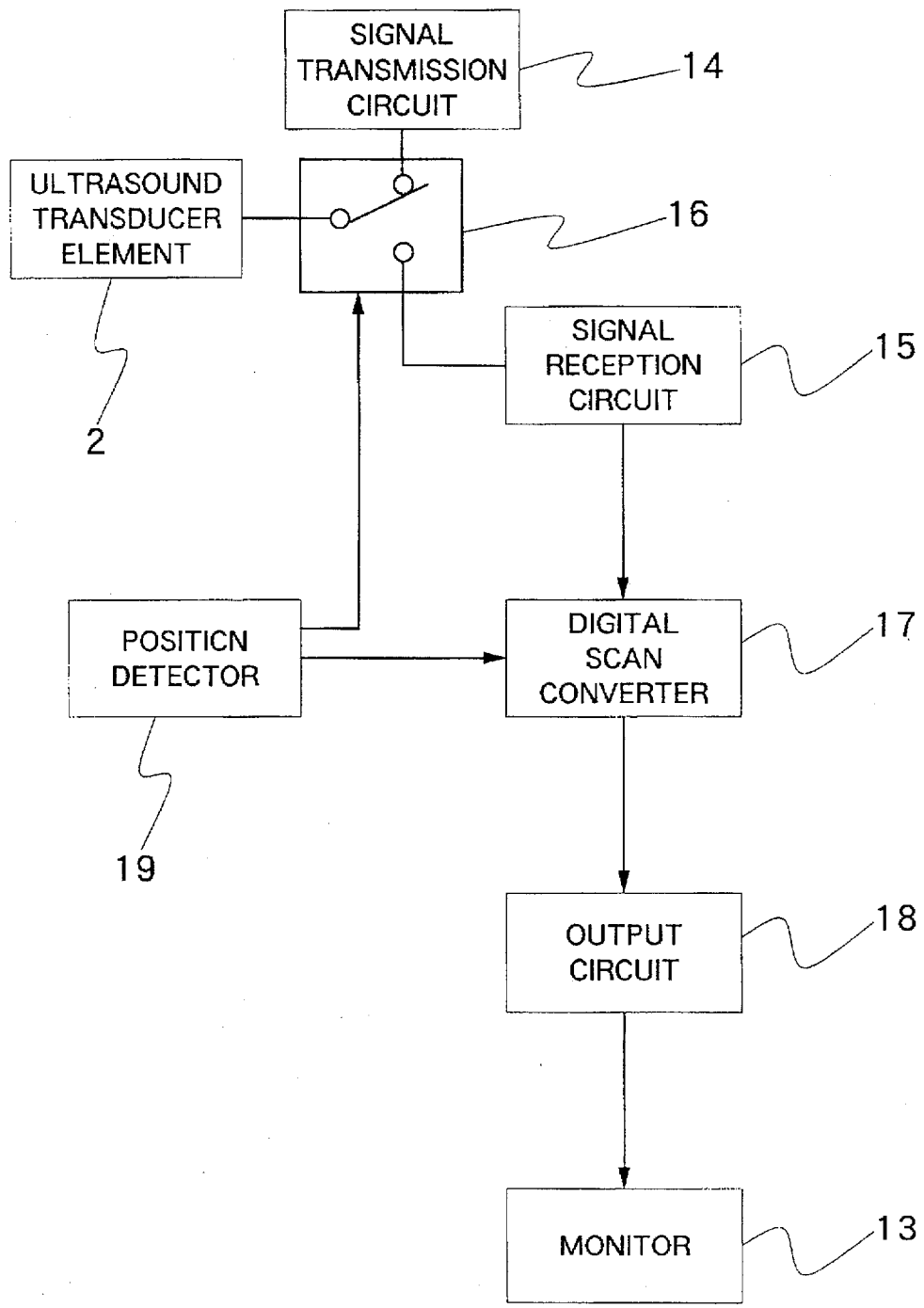
FIG. 3 is a circuit diagram of a signal processor.

Firstly, as shown particularly in FIG. 4, the scanner head assembly 1 is held against the body of a patient, with the cap 4 of the ultrasound transducer element 2 in contact with an outer skin surface of a scanning region. Preferably, ultrasound jelly or the like is applied on the skin surface of the scanning region beforehand to ensure intimate contact between the scanning skin surface and the cap 4. Since the tracking roller portion 8a of the hollow rotary shaft 8 is provided in the proximity of the cap 4, it is also held in intimate contact with the scanning body surface of the patient. In order to make a linear ultrasound scan by the ultrasound transducer element 2, the operator grips the scanner head 1 and moves it in a direction of particular interest. As the scanner head 1 is moved in this manner, the tracking roller portion 8a of the hollow rotational shaft 8 is turned by contact with the body surface scanned by the ultrasound transducer element 2, and the angle of rotation of the hollow rotational shaft 8 is concurrently detected by the encoder 9 to supply a position signal to the position detector circuit 19.

At predetermined intervals in travel distance of the ultrasound transducer element 2, switching signals are supplied from the position detector circuit 19 to the switch means 16 to connect the transducer element 2 alternately with the transmission circuit 14 and the reception circuit 15. As soon as the connection is switched to the signal transmission circuit 14, the ultrasound transducer element 2 is thereby driven to transmit an ultrasound pulse signal into the body of the patient. Concurrently with the signal transmission, a position signal which is required for generation of an ultrasound picture image, are sent to the digital scan converter 17 from the position detector circuit 19. After transmitting an ultrasound pulse signal into an intracorporeal region of interest, the operation is switched to a reception phase by the switch means 16, connecting the ultrasound transducer element 2 to the reception circuit 15 for reception of return echoes of the transmitted ultrasound signal. Electrical signals of received return echoes are fed to and converted into video signals by known signal processing operations at the reception circuit 15, and then supplied to the frame memory of the digital scan converter 17 along with position signals from the position detector circuit 19.

In this manner, while the ultrasound scanner head 1 is being moved for a scanning operation, the transmission and reception of ultrasound signals are alternately repeated at predetermined intervals in travel distance of the ultrasound transducer element 2 in step with the mechanical linear scan over a given range. As soon as video signals for one frame of ultrasound picture image are collected in the frame memory of the digital scan converter 17, they are supplied to the monitor 13 from the video output circuit 18 to display an ultrasound picture image on the monitor screen 13.

In order to detect the scanning position of the ultrasound transducer element 2 correctly, the tracking roller portion 8a of the hollow rotational shaft 8 is positioned in the close proximity of the ultrasound transducer element 2 and associated therewith rigidly to follow the movements of the transducer element 2 securely in a reliable manner. Besides, the position detection mechanism, which is constituted by the hollow rotational shaft 8 and the encoder 9 as described above, is simple and compact in construction and light in weight, permitting the operator to handle the scanner head extremely easily in scanning operations. Accordingly, in case of making linear ultrasound scans targeted at a certain intracorporeal region, the operator can easily move the ultrasound scanner head 1 to and fro along and in contact with the body surfaces of the target scanning region.

Figure 5:
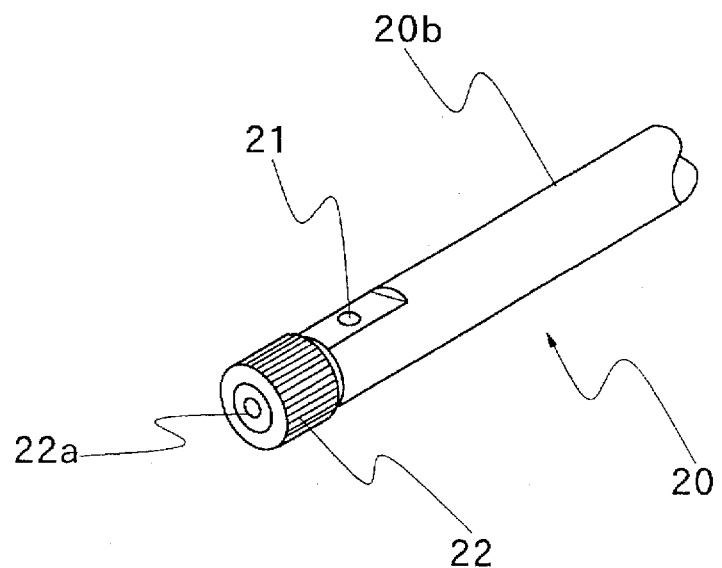
FIG. 5 is a fragmentary outer view of a scanner head assembly adopted as a second embodiment of the invention.
Figure 6:
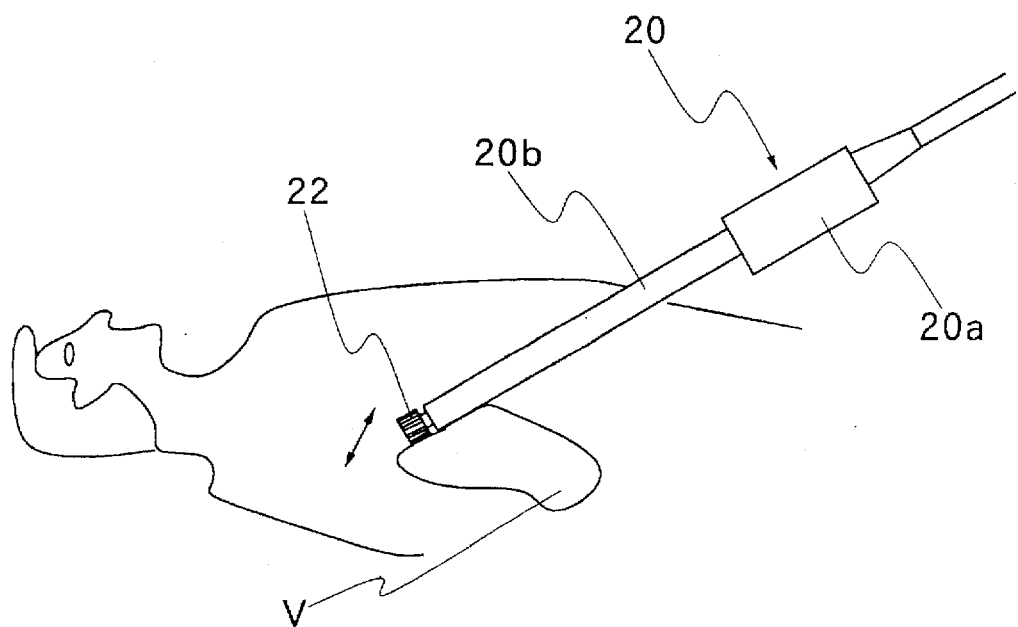
FIG. 6 is a schematic illustration of a scanning operation by the use of the ultrasound scanner of the second embodiment.

Referring now to FIGS. 5 and 6, there is shown a second embodiment of the invention, employing an ultrasound scanner head 20 which is arranged to be inserted into an abdominal cavity or the like to make ultrasound scans along surfaces of an internal organ.

In this case, the ultrasound scanner head assembly 20 is provided with an elongated rod-like tubular extension 20b on the front side of a main casing 20a. The rod-like tubular extension 20b is provided with a notched portion at one side of its fore end portion to nest an ultrasound transducer element 21 therein. A rotary tracking member in the form of a rotary tracking wheel 22 is rotatably supported on the front side of the distal end face of the rod-like tubular extension 20b. The tracking wheel 22 is provided on a distal fore end portion of a rotational shaft 22a which is, similarly to the hollow rotational shaft 8 of the foregoing first embodiment, passed through the rod-like tubular extension 20b and led into the main casing 20a of the scanner head assembly 20 to transmit its rotation to an encoder (not shown) which is provided in the main casing 20a substantially in the same manner as in the first embodiment.

With the arrangements just described, the rod-like tubular extension 20b of the scanner head 20 is introduced into an abdominal cavity of a patient as shown in FIG. 6, and the fore end of the tubular extension 20b with the ultrasound transducer element 21 is moved along the surface of an internal organ of interest, for example, along the surface of the liver in the arrowed directions. During this movement, the rotary wheel 22 is turned through an angle in proportion to the distance of movement of the transducer element 21. Accordingly, in a manner similar to the foregoing first embodiment, the position or distance of movement of the ultrasound transducer element 21 in each linear scanning stroke can be detected on the basis of signals from the rotary encoder which is coupled with the rotational shaft 22.

Figure 7:
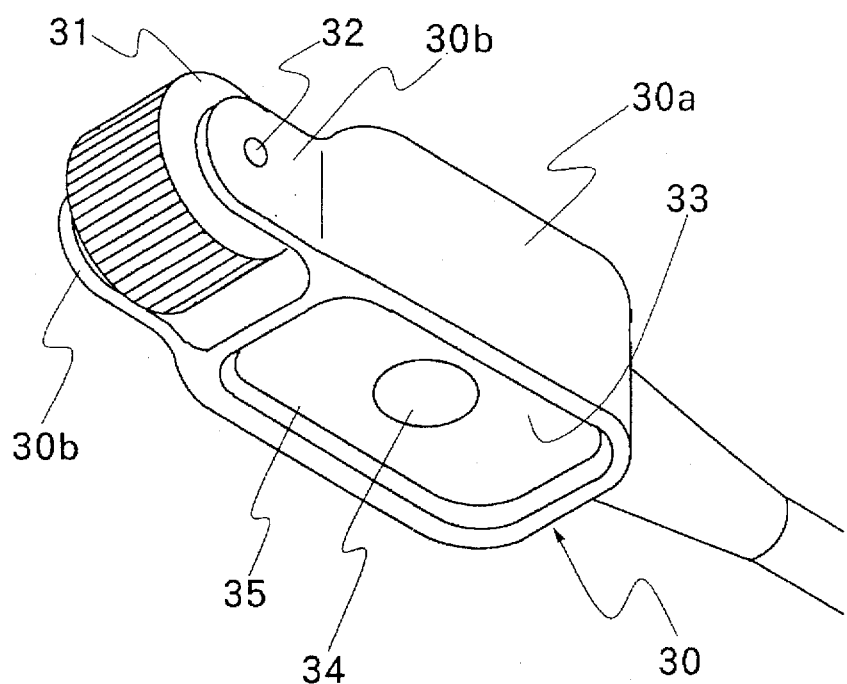
FIG. 7 is a schematic outer view from beneath of a scanner head assembly adopted as a third embodiment of the invention.
Figure 8:
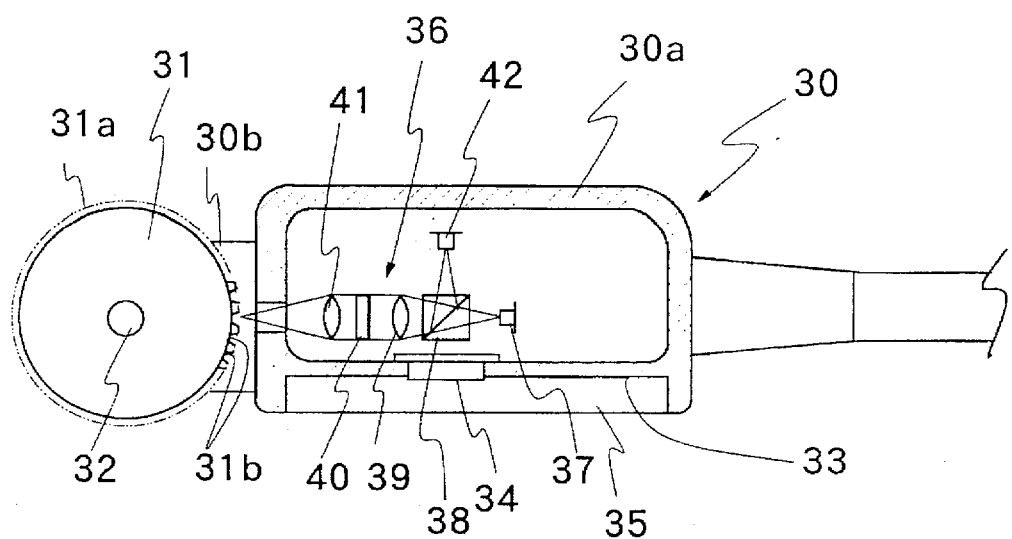
FIG. 8 is a schematic sectional view of the scanner head assembly of FIG. 7.

Illustrated in FIGS. 7 and 8 is a third embodiment of the present invention, employing an ultrasound scanner head assembly 30 with a tracking roller 31 which is rotatably supported on the front side of its main casing 30a. More specifically, the tracking roller 31 has its axle 32 journalled on a pair of brackets 30b which are provided opposingly on the front side of the main casing 30a. On the other hand, an ultrasound transducer element 34 is fixedly anchored in a recessed bottom wall 33 on the lower side of the main casing 30 of the scanner head 30. Fitted in the recessed portion on the lower side of the main casing 30a is an ultrasound gel pad 35 of an ultrasound transmissive medium such as Aquaflex (a product name of Parker Laboratories Inc.) or other gel material which has satisfactory properties in ultrasound transmission and which is deformable in conformity with undulations or contours on body surfaces to be scanned. The ultrasound transmissive pad 35 of this sort serves to provide a stand-off margin between the ultrasound transducer element 34 and a scanning body surface and to guarantee efficient transmission and reception of ultrasound signals.

As means for detecting the position or distance of movement of the ultrasound transducer element 34 on the scanner head assembly 30, this embodiment employs a position measuring mechanism incorporating an optical detector means for detecting rotational angles of the tracking roller 31. More specifically, as shown particularly in FIG. 8, the tracking roller 31 is provided with a multitude of uniformly spaced optically detectible graduation means 31b around its circumferential treading surface 31a, in this particular embodiment, a multitude of axial grooves and ridges which are formed alternately at uniform intervals in the rotational direction of the tracking roller 31, in face to face relation with an optical detector means 36. The just mentioned optical detector means 36 is located on the front side of the main casing 30a between the brackets 30b, and internally provided with a laser diode 37 as a light source. A laser light beam from the laser diode 37 is passed through a beam splitter 38 and collimated through a collimator lens 39. Then, through a quarter-wave plate 40 and an objective lens 41, the collimated light beam is focused on the treading surface 31a of the roller 31. Light reflections off the treading surface 31a of the roller 31 are passed back through the objective lens 41, quarter-wave plate 40 and collimator lens 39, and reflected on the beam splitter 38 toward a photo-detector 42 which is faced toward the light reflecting surface of the beam splitter 38.

The photo-detector 42 is located at the back focal position of the objective lens 40, so that reflections of light rays, which have been converged through the objective lens 40 to focus on the treading surface 31a of the roller 31, are totally received by the photo-detector 42. On the other hand, when light rays from the objective lens 40 are reflected from a point within a detection groove 31b, which is in a defocussed position, the amount of light reflections received by the photo-detector 42 is reduced to an extent corresponding to the deviation of the reflecting surface from the focal point of the objective lens 40. Accordingly, as the tracking roller 31 is turned to follow movement of the ultrasound scanner head 30 along a scanning body surface of a patient, the intensity of light incident on the photo-detector 42 varies cyclically according to the rotational angle of the tracking roller 31, giving signals indicative of the position or the distance of movement of the ultrasound transducer element 34 in each scanning operation by the scanner head 30.

Figure 9:
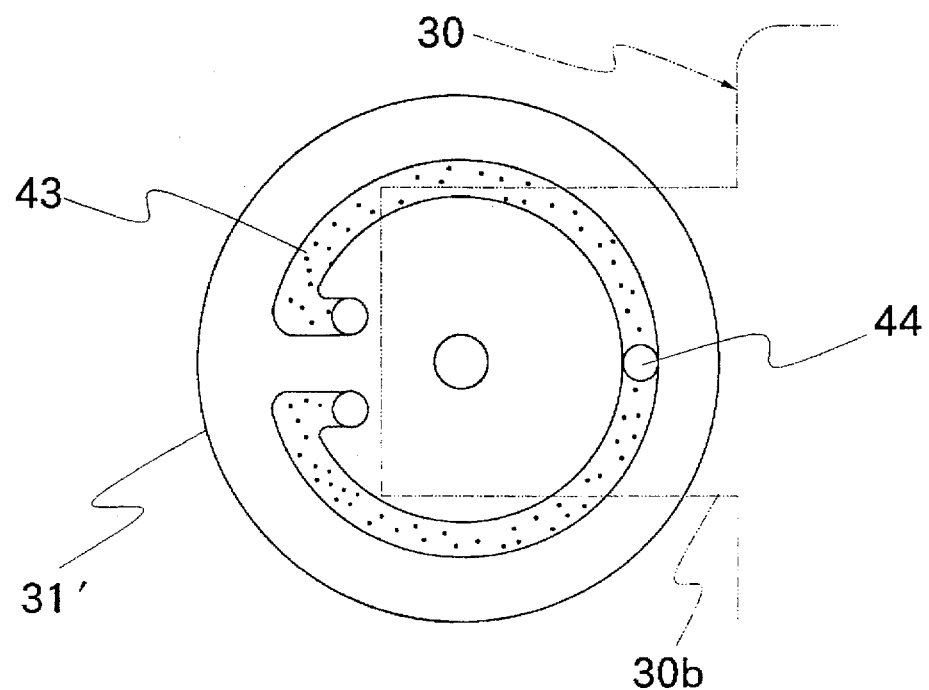
FIG. 9 is a schematic view of a position detector mechanism employed in the third embodiment of FIG. 7.

Alternatively, in order to detect the rotational angle of a tracking roller of the sort similar to the roller 31 described above, there may be employed the so-called potentiometer type position detector mechanism including, as shown in FIG. 9, an arcuate resistor strip 43 fixed on an end face of a tracking roller 31' and an electrode 44 mounted opposingly on one bracket 30b of the scanner head 30 in sliding contact with the arcuate resistor strip 43.

Figure 10:
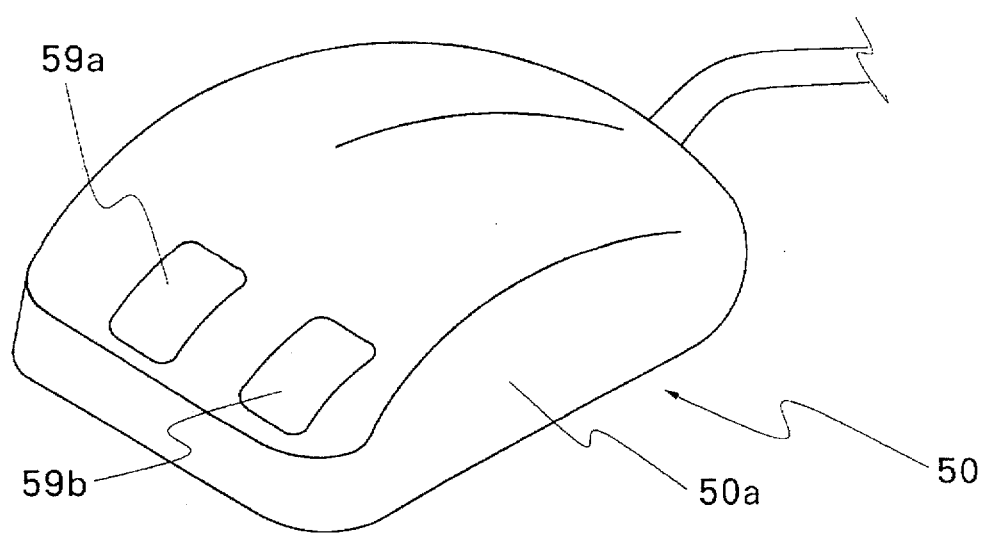
FIG. 10 is a schematic perspective view of another position detector mechanism useful in the third embodiment.
Figure 11:
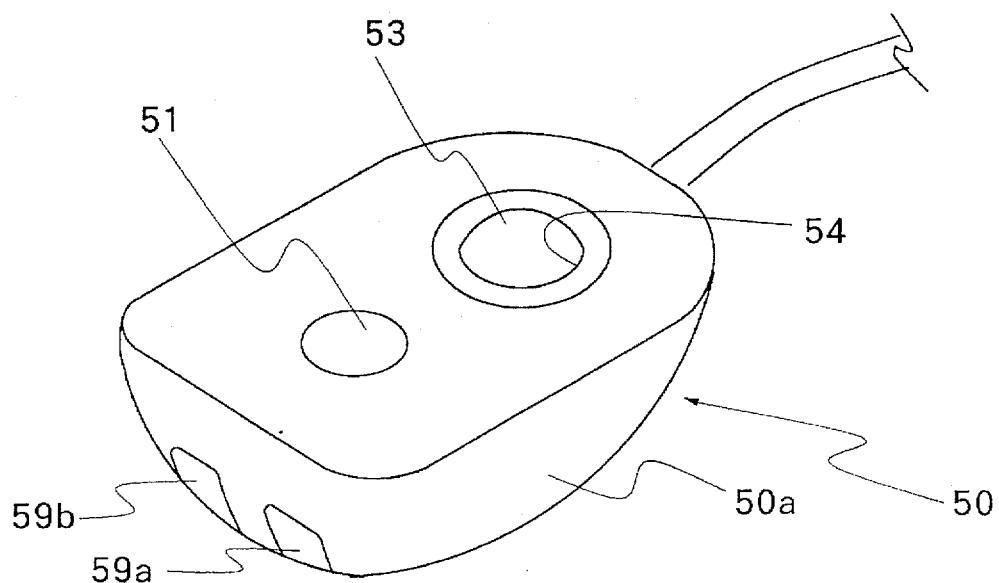
FIG. 11 is a schematic bottom view of a scanner head assembly adopted as a fourth embodiment of the invention.
Figure 12:
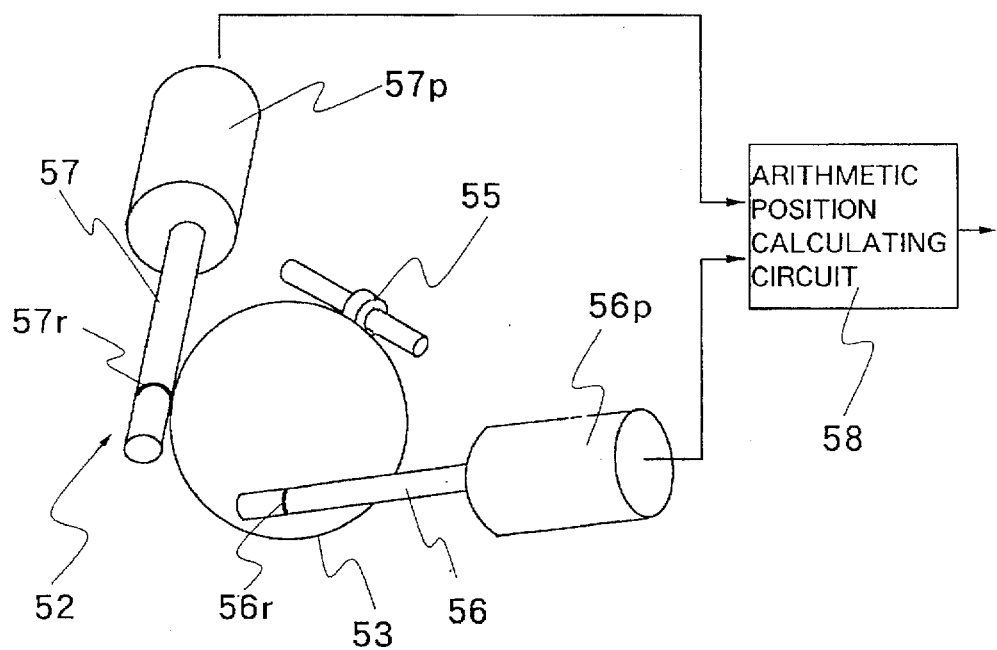
FIG. 12 is a schematic illustration explanatory of operating principles of an X- and Y-axis movement detection mechanism.

Illustrated in FIGS. 10 to 12 is a fourth embodiment of the invention employing an ultrasound scanner head 50 which can be moved with greater freedom in arbitrary directions in mechanical scanning operations. Namely, the ultrasound scanner head 50 of this embodiment can be moved not only along a straight line but also along a curved line, in contrast to the foregoing first to third embodiments in which the scanning direction is determined by the direction of the rotational axis of the rotary tracking member.

More specifically, as shown particularly in FIGS. 10 and 11, the ultrasound scanner head 50 is housed in a casing 50a which is so shaped as to be suitably gripped in a hand of an operator. An ultrasound transducer element 51 is mounted on the lower side of the scanner head casing 50a along with an X- and Y-axis displacement detector mechanism 52 which is arranged to detect displacements of the ultrasound transducer element 51 in the directions of X- and Y-axes. As seen in FIGS. 11 and 12, the X- and Y-axis displacement detector mechanism 52 employs a steel ball 53 which is urged to protrude partly on the outer side through an aperture 54 in the bottom wall of the scanner head casing 50a and to turn in the same direction as the scanner head 50 is moved by an operator for a scanning operation with the bottom side of the scanner head casing 50a in sliding contact with a scanning body surface of a patient. By the action of a biasing roller 55, the steel ball 53 is urged into abutting engagement with X- and Y-axis shafts 56 and 57 to cause the latter to turn therewith depending upon the distance and direction of movement of the scanner head 50. The X- and Y-axis shafts 56 and 57 are coupled with X- and Y-axis potentiometers 56P and 57P, thereby to detect rotational angles of the X- and Y-axis shafts 56 and 57, respectively. For the purpose of ensuring smooth transmission and reception of ultrasound signals, the scanner head 50 may employ a pad of ultrasound transmissive medium of the nature as described hereinbefore in connection with the third embodiment of the invention. In case ultrasound jelly is applied on a scanning body surface of a patient in place of a pad just mentioned, there may arise a problem of slips of the steel ball 54 on the jelly-applied body surface, failing to transmit movements of the ultrasound transducer element to the X- and Y-axis shafts 56 and 57. In order to solve a problem of this sort, the steel ball 53 may have a surface which is frictionally coarsened to a certain degree or which is laminated with a material with a higher friction coefficient like rubber, in addition to the use of anti-slip means on the part of the X- and Y-axis shafts 56 and 57, for example, rubber rings 56r and 57r which are fitted on those circumferential areas of the X- and Y-axis shafts 56 and 57 to be held in abutting engagement with the steel ball 53.

In this case, the ultrasound scanner head 50 can be moved in an arbitrary direction along a body surface of a scanning region, and the steel ball 53 is turned according to the distance and direction of movement of the scanner head 50. The rotation of the steel ball 53 is followed by the X- and Y-axis shafts 56 and 57 which resolve or decompose the movements of the ultrasound transducer element 51 on the scanner head 50 into displacements in the X- and Y-axis directions. The movements in the X- and Y-axis directions are picked up by X- and Y-axis potentiometers 56P and 57P, respectively, and resulting signals are fed to an arithmetic position calculating circuit 58. Indicated at 59a and 59b are push button switches which are provided on the casing 50a of the scanner head 50, for example, for starting and stopping a video tape recorder which is provided on the ultrasound image observation terminal of the examination system for recording ultrasound images.

Accordingly, for example, at a point where displacement signals $\Delta x$ and $\Delta y$ are produced by the X- and Y-axis potentiometers 56P and 57P, it means that the ultrasound transducer element 51 has been moved over a distance corresponding to the square root of $\Delta x^2+\Delta Y^2$, and the transducer position is determined by calculations based on this formula at the arithmetic calculation circuit 58, which produces a switching signal at predetermined intervals in travel distance of the ultrasound transducer element 51 for supply to the afore-mentioned switch means which connects the transducer element 51 alternately with the signal transmission circuit and the signal reception circuit, in addition to a position signal to be supplied to the digital scan converter, in the same manner as in the first embodiment shown hereinbefore.

With the arrangements just described, the ultrasound scanner head 50 can be moved in an arbitrary direction along a body surface of a scanning region, permitting to set the ultrasound transducer element 51 in a scanning movement freely in any desired direction at any point of scanning stroke. Accordingly, it becomes possible to move the ultrasound scanner head 50, for example, along a curved line which corresponds to the shape or contour of an internal organ of interest, for the purpose of obtaining tomographic ultrasound images along a subject of interest which is actually in a curved shape.

As clear from the foregoing description, for detection of the position of an ultrasound transducer element in linear scanning operations, the ultrasound scanner head according to the present invention is provided with a rotary tracking member which is rotatable in proportion to the distance of travel of an ultrasound transducer element on the scanner head, in combination with a position measuring means which detects the position of the transducer element on the basis of rotational angle of the rotary tracking member. Thus, according to the present invention, the position signals, which are necessary for controlling the signal transmission and reception phases of the ultrasound transducer element as well as for determining positions of the respective acoustic lines in the generation of ultrasound images, can be obtained by the use of a mechanism which is extremely simple and compact in construction and at the same time significantly light in weight.

What is claimed is:

1. An mechanical scan type ultrasound scanner head for ultrasound examination systems, said scanner head comprising:

an ultrasound scanner head assembly movable along a subject to be ultrasonically scanned;

an ultrasound transducer element mounted on said ultrasound scanner head assembly to transmit and receive ultrasound signals at predetermined intervals while said scanner head assembly is moved along said subject for a scanning operation;

a rotary tracking member mounted on said scanner head assembly in the proximity of said ultrasound transducer element for rotation about an axis fixed relative to and at a rate commensurate with the distance of movement of said ultrasound transducer element; and a position measuring means connected to said rotary tracking member to measure the distance of travel of said ultrasound transducer element from an initial position of a scanning operation by way of rotational angle of said rotary tracking member.

2. A mechanical scan type ultrasound scanner head as defined in claim 1, wherein said rotary tracking member is in the form of a cylindrical tracking roller provided at the fore end of a rotational shaft, and said position measuring means is constituted by an encoder mounted on said scanner head assembly and coupled with said rotational shaft through transmission gears.

3. A mechanical scan type ultrasound scanner head as defined in claim 1, wherein said rotary tracking member is in the form of a tracking roller journalled on the front side of said scanner head assembly.

4. A mechanical scan type ultrasound scanner head as defined in claim 3, wherein said tracking roller is provided with optically detectible grooves at uniformly spaced positions around a circumferential treading surface, and said position measuring means is constituted by an optical detector mounted on said scanner head assembly in face to face relation with said circumferential treading surface to detect a rotational angle of said tracking roller by way of said optically detectible grooves.

5. A mechanical scan type ultrasound scanner head as defined in claim 3, wherein said position measuring means is constituted by a potentiometer mounted on said scanner head assembly in contact with a resistor member provided on said tracking roller.

6. A mechanical scan type ultrasound scanner head as defined in claim 1, wherein said rotary tracing member is in the form of a steel ball partly protruded on the lower side of said scanner head assembly, and said position measuring means is constituted by an X- and Y-axis displacement detector mechanism including X- and Y-axis shafts held in abutting contact with said steel ball in such a manner as to be rotated about the respective axes according to rotational movements of said steel ball.

7. A mechanical scan type ultrasound scanner head as defined in claim 1, wherein said ultrasound transducer element is nested on a projected support member at the fore end of a main casing of said ultrasound scanner head assembly, and said rotary tracking member is rotatably mounted on said main casing side by side with said ultrasound transducer for rotation about an axis substantially perpendicular to a scanning direction by said scanner head.

8. A mechanical scan type ultrasound scanner head as defined in claim 7, wherein said ultrasound transducer element on said projected support member is enclosed in a cap member internally filled with an ultrasound transmissive medium, and said rotary tracking member is in the form of a tracking roller rotatably fitted around said projected support member and operatively coupled with said position measuring means.

9. A mechanical scan type ultrasound scanner head for ultrasound examination systems, said scanner head comprising an ultrasound scanner head assembly movable along a subject to be ultrasonically scanned;

an ultrasound transducer element mounted on said ultrasound scanner head assembly to transmit and receive ultrasound signals at predetermined intervals while said scanner head assembly is moved along said subject for a scanning operation;

a rotary tracking member mounted on said scanner head assembly in the proximity of said ultrasound transducer element for rotation about an axis fixed relative to and at a rate commensurate with the distance of movement of said ultrasound transducer element; and a position measuring means connected to said rotary tracking member to measure the distance of travel of said ultrasound transducer element from an initial position of a scanning operation by way of a rotational angle of said rotary tracking member;

said rotary tracking member being in the form of a steel ball partly protruded on the lower side of a casing of said scanner head assembly; and said position measuring means being constituted by an X- and Y-axis shafts held in abutting contact with said steel ball in such a manner as to be rotated about the respective axes according to rotational movements of said steel ball.

10. A mechanical scan type ultrasound scanner head as defined in claim 9, wherein said ultrasound scanner head is provided with at least one push-button switch on said casing.

* * * * *